United States Patent
Popovic et al.

(10) Patent No.: US 11,266,473 B2
(45) Date of Patent: *Mar. 8, 2022

(54) SENSORLESS FORCE CONTROL FOR TRANSESOPHAGEAL ECHOCARDIOGRAPHY PROBE

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 20 days.

This patent is subject to a terminal disclaimer.

(21) Appl. No.: 16/357,792

(22) Filed: Mar. 19, 2019

(65) Prior Publication Data
US 2019/0209254 A1 Jul. 11, 2019

Related U.S. Application Data

(63) Continuation of application No. 15/112,707, filed as application No. PCT/IB2015/050302 on Jan. 15, 2015, now Pat. No. 10,258,417.
(Continued)

(51) Int. Cl.
*A61B 1/31* (2006.01)
*A61B 34/30* (2016.01)
(Continued)

(52) U.S. Cl.
CPC .......... *A61B 34/37* (2016.02); *A61B 1/0016* (2013.01); *A61B 1/00039* (2013.01);
(Continued)

(58) Field of Classification Search
CPC ......... A61B 34/37; A61B 1/31; A61B 8/0883; A61B 8/12; A61B 34/30; A61B 1/00039; A61B 1/00057; A61B 1/0016; A61B 2034/301; A61B 2090/065; A61B 2017/00725; A61B 1/00006;
(Continued)

(56) References Cited

U.S. PATENT DOCUMENTS 5,469,840 A 11/1995 Tanii
5,609,563 A 3/1997 Suzuki
(Continued)

FOREIGN PATENT DOCUMENTS

JP 4263830 A 9/1992
JP 5300873 A 11/1993

*Primary Examiner* — Robert T Nguyen

(57) ABSTRACT

A robotic actuation system for sensorless force control of an interventional tool (14) having cable driven distal end (e.g., a probe, a steerable catheter, a guidewire and a colonoscope). The system employs a robotic actuator (30) having one or more motorized gears operate the cable drive of the interventional tool (14). The system further employs a robotic workstation (20) to generate motor commands for simultaneous actuation position and contact force control of the interventional tool (14). The motor commands are a function of an actuation position measurement and a motor current measurement of the at least one motorized gear for a desired actuation position of the interventional tool (14).

9 Claims, 8 Drawing Sheets

Related U.S. Application Data

(60) Provisional application No. 61/931,203, filed on Jan. 24, 2014.

(51) Int. Cl.
| | |
|---|---|
| *A61B 90/00* | (2016.01) |
| *A61B 1/00* | (2006.01) |
| *A61B 34/37* | (2016.01) |
| *A61B 8/08* | (2006.01) |
| *A61B 8/12* | (2006.01) |
| *A61M 25/01* | (2006.01) |
| *A61M 25/09* | (2006.01) |
| *A61B 1/005* | (2006.01) |
| *A61B 17/00* | (2006.01) |

(52) U.S. Cl.
CPC ............ *A61B 1/00057* (2013.01); *A61B 1/31* (2013.01); *A61B 8/0883* (2013.01); *A61B 8/12* (2013.01); *A61B 34/30* (2016.02); *A61M 25/0116* (2013.01); *A61M 25/09041* (2013.01); *A61B 1/00006* (2013.01); *A61B 1/0051* (2013.01); *A61B 2017/00725* (2013.01); *A61B 2034/301* (2016.02); *A61B 2090/065* (2016.02)

(58) Field of Classification Search
CPC ............ A61B 1/0051; A61M 25/0116; A61M 25/09041; B25J 9/1633; B25J 9/1692
See application file for complete search history.

(56) References Cited

U.S. PATENT DOCUMENTS

| | | | | |
|---|---|---|---|---|
| 9,393,068 | B1* | 7/2016 | Leo | A61B 34/10 |
| 2002/0180279 | A1* | 12/2002 | Faizullabhoy | H02K 41/03 |
| | | | | 310/12.19 |
| 2005/0150123 | A1* | 7/2005 | Eaton | G01B 5/004 |
| | | | | 33/503 |
| 2008/0314654 | A1* | 12/2008 | Dodgson | G06F 3/045 |
| | | | | 178/18.05 |
| 2009/0088775 | A1* | 4/2009 | Swarup | A61B 34/30 |
| | | | | 606/130 |
| 2010/0076263 | A1* | 3/2010 | Tanaka | A61B 1/00158 |
| | | | | 600/109 |
| 2010/0160728 | A1* | 6/2010 | Yoshie | A61B 1/00147 |
| | | | | 600/109 |
| 2010/0204547 | A1* | 8/2010 | Tanaka | A61B 5/06 |
| | | | | 600/145 |
| 2010/0268031 | A1 | 10/2010 | Koyama | |
| 2010/0298826 | A1* | 11/2010 | Leo | A61B 18/1492 |
| | | | | 606/41 |
| 2011/0015786 | A1* | 1/2011 | Kawai | A61B 1/0016 |
| | | | | 700/256 |
| 2011/0106141 | A1* | 5/2011 | Nakamura | A61B 34/30 |
| | | | | 606/205 |
| 2011/0153252 | A1 | 6/2011 | Govari | |
| 2011/0275892 | A1* | 11/2011 | Tanaka | A61B 1/0016 |
| | | | | 600/109 |
| 2011/0282154 | A1* | 11/2011 | Umemoto | A61B 5/065 |
| | | | | 600/152 |
| 2011/0295063 | A1 | 12/2011 | Umemoto | |
| 2013/0006268 | A1 | 1/2013 | Swarup | |
| 2013/0217965 | A1* | 8/2013 | Sasamoto | A61B 1/018 |
| | | | | 600/109 |
| 2013/0221887 | A1* | 8/2013 | Aghili | H02P 6/10 |
| | | | | 318/400.23 |
| 2014/0005718 | A1* | 1/2014 | Shelton, IV | A61B 34/35 |
| | | | | 606/205 |
| 2014/0031626 | A1* | 1/2014 | Schwarz | A61B 1/018 |
| | | | | 600/149 |
| 2014/0312227 | A1* | 10/2014 | Yoshikawa | H01J 37/285 |
| | | | | 250/310 |
| 2015/0168496 | A1* | 6/2015 | Moura | G01L 3/22 |
| | | | | 702/182 |
| 2016/0197568 | A1* | 7/2016 | Sung | H02P 6/18 |
| | | | | 318/400.13 |
| 2017/0079644 | A1* | 3/2017 | Overmyer | A61B 17/068 |
| 2018/0116749 | A1* | 5/2018 | Wu | B25J 9/163 |

\* cited by examiner

SENSORLESS FORCE CONTROL FOR TRANSESOPHAGEAL ECHOCARDIOGRAPHY PROBE

CROSS-REFERENCE TO PRIOR APPLICATIONS

This application is a continuation application of Ser. No. 15/112,707, filed Jul. 20, 2016, which is the U.S. National Phase application under 35 U.S.C. § 371 of International Application No. PCT/IB2015/050302, filed on Jan. 15, 2015, which claims the benefit of U.S. Provisional Patent Application No. 61/931,203, filed on Jan. 24, 2014. These applications are hereby incorporated by reference herein.

The present invention generally relates to transesophageal echocardiography ("TEE") probes. The present invention specifically relates to sensorless force control of the TEE probe during an interventional procedure.

Transesophageal echocardiography is commonly used to visualize cardiac anatomy and interventional devices during treatment for structural heart disease ("SHD"). FIG. 1 shows a typical distribution of theatre staff within a lab room 10 having an ultrasound workstation 11 and an x-ray scanner, of which a c-arm 12 is shown. During a KID operation, an echocardiographer 13 holds a TEE probe 14, which passes through a mouth of a patient 16 into an esophagus to visualize a heart of patient 16. A cardiologist 15 is located on an opposite side of x-ray c-arm 12 and an operating table 17. Cardiologist 15 navigates interventional devices (not shown) (e.g., catheters and guidewires) from arterial incisions into the heart under x-ray guidance and ultrasound guidance via TEE probe 14 in order to perform different diagnostic or therapeutic procedures. Exemplar procedures, such as mitral clip deployments or transcatheter aortic valve replacements ("TAVR"), can be time consuming and complex. Moreover, ensuring appropriate visualization of the target anatomy during the procedure is the responsibility of echocardiographer 13, who must make constant small adjustments to a position of a tip of TEE probe 14 for the duration of the procedure.

In practice, the operating conditions of FIG. 1 present several challenges. The first challenge is fatigue and poor visualization. Specifically, appropriate visualization includes both ensuring the relevant anatomical structures are within the field of view, and that the necessary contact force between the transducer head and esophageal wall, to achieve adequate acoustic coupling, is achieved. To this end, a position and an orientation of a head of TEE probe 14 requires constant, minute adjustments for the duration of the procedure in order to maintain appropriate visualization of the target structures. This can lead to fatigue and poor visualization by echocardiographer 13 during long procedures.

The second challenge is x-ray exposure. Specifically, a length of TEE probe 14 results in the positioning of echocardiographer 13 in close proximity to the source of interventional x-ray system, thus maximizing the x-ray exposure of echocardiographer 13 over the course of the procedure.

The third challenge is communication and visualization. During certain phases of a procedure, cardiologist 15 and echocardiographer 13 must be in constant communication as cardiologist 15 instructs echocardiographer 13 as to which structure to visualize. Given the difficultly interpreting a 3D ultrasound volume, and the different co-ordinate systems displayed by the x-ray and ultrasound systems, it can be challenging for echocardiographer 13 to understand the intentions of cardiologist 15.

The present invention provides a robotic actuation system to address these challenges. Generally, as shown in FIG. 2, a new distribution of theatre staff within a lab room 10b with the robotic actuator system employing a robotic workstation 20 and robotic actuator 30 for remote control of between two (2) degrees of freedom and (4) degrees of freedom of TEE probe 14 which adjust the ultrasound imaging volume of TEE probe 14. Additionally, as will be further described herein, robotic actuator 30 may have the ability to be retrofitted to existing and various types of TEE probe 14 and may have the ability to be rapidly remove from TEE probe 14 should echocardiographer 13 decide to return to manual operation of TEE probe 14 for any reason.

A potential issue however arising from robotic control of TEE probe 14 is safety. Specifically, as the dials of TEE probe 14 are moved by rotor actuator 30 and not by hand of echocardiographer 13, then there is no haptic feedback (i.e., echocardiographer 13 cannot feel if the probe 14 is exerting excessive forces on the esophagus of patient 16).

Force control of robots is known in art in applications such as grinding or assembly. These methods use force sensors to detect force or torque on the robot end-effector or in the robot joints. Similarly, probe-tissue contact force may be measured with force sensors known in art. However, there are several issues with measuring probe-tissue contact force with force sensors.

First, TEE probe 14 has to be modified to include the force sensors. For safety and comfort of patient 16, the size of TEE probe 14 has to be as small as possible. Conversely, for guidance and diagnostic purposes, the imaging element of TEE probe 14 has to be as large as possible to increase the field-of-view. With these constraints, adding new electronics to the head of TEE probe 14 may interfere with the main function of TEE probe 14, which is the acquisition of ultrasound images.

Second, the sensors can only be placed at discrete locations of TEE probe 14, whereas an injury to patient 16 may occur at any point along a length of the entire TEE probe 14.

Third, if direct force sensing is used, then any force sensor based control system may only be used with the newly manufactured probes only. However, it would be beneficial to use a force control system with TEE probes 14 already deployed in the field.

Sensor-less force control is also known in art where the force is inferred from other parameters of the system, most typically current in the motors. In traditional robotic applications, the force and position are decoupled. In these applications, the control scheme combines path control and force control. For example, the path control loop can control the process in non-compliant mode while the force control loop can control the system in the compliant mode. These dual loops can also run concurrently. Furthermore, in traditional robotic applications, the current in the motor of end-effector does not depend on the position of the entire robot which simplifies sensor-less force control.

The problem of force-control of TEE probe 14 is unique to the family of devices that are cable-driven (e.g., TEE ultrasound probes and catheters) because the entire actuation is done at the proximal end of TEE probe 14 leading to a couple of issues. First, forces sensed or measured in the motors of robotic actuator 30 will depend on the force the TEE probe 14 is exerting on the tissues as well as on the shape of the entire length of TEE probe 14. Second, force sensed or measured in motors of robotic actuator 30 includes force needed to pull cables. This force will vary depending on position of the head of TEE probe 14.

The present invention provides sensor-less force control of TEE probe 14 by robotic workstation 20 processing a simultaneous tip position/force estimate of TEE probe 14 from robotic actuator 30. This allows a safe remote manipulation of TEE probe 14, thereby reducing the risk of injury to an esophagus of patient 16, and allows robotic workstation 20 and robotic actuator 30 to be utilized with the probes already deployed in the field.

One form of the present invention is a robotic actuation system for sensorless force control of an interventional tool having a cable driven distal end (e.g., a probe, a steerable catheter, a guidewire and a colonoscope). The system employs a robotic actuator having one or more motorized gears to operate the cable drive of the interventional tool. The system further employs a robotic workstation to generate motor commands for simultaneous actuation position and contact force control of the interventional tool. The motor commands are a function of an actuation position measurement and a motor current measurement of the at least one motorized gear for a desired actuation position of the interventional tool.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 6A:
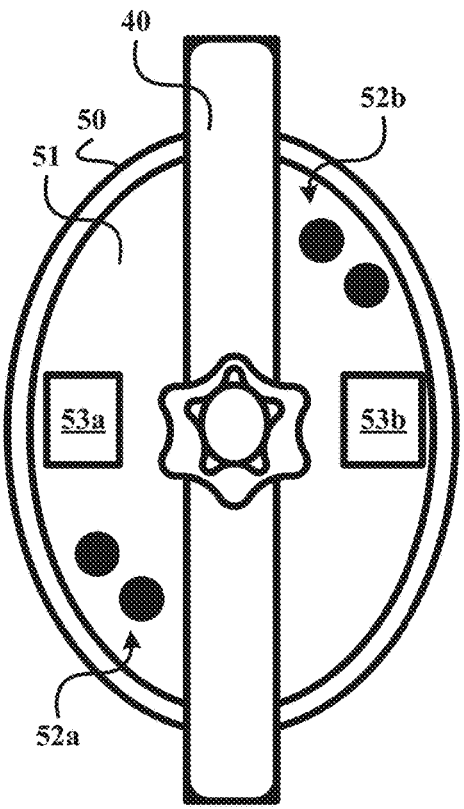
Figure 6B:
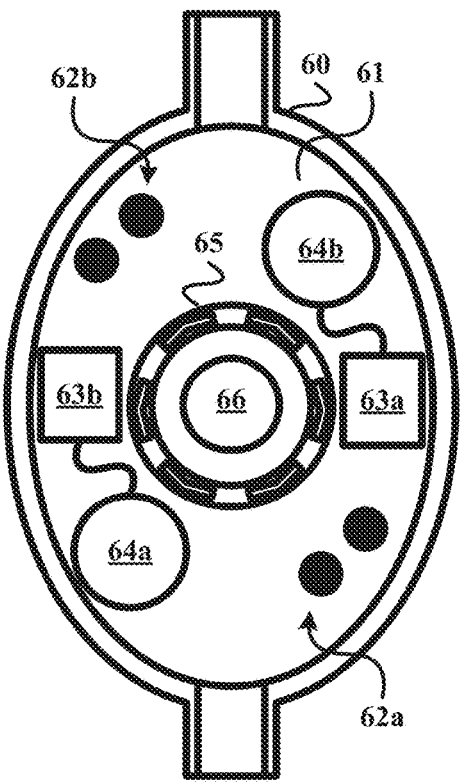

FIGS. 6A and 6B respectively illustrate exemplary embodiments of a probe handle base and a probe handle cover in accordance with the present invention.

Figure 7:
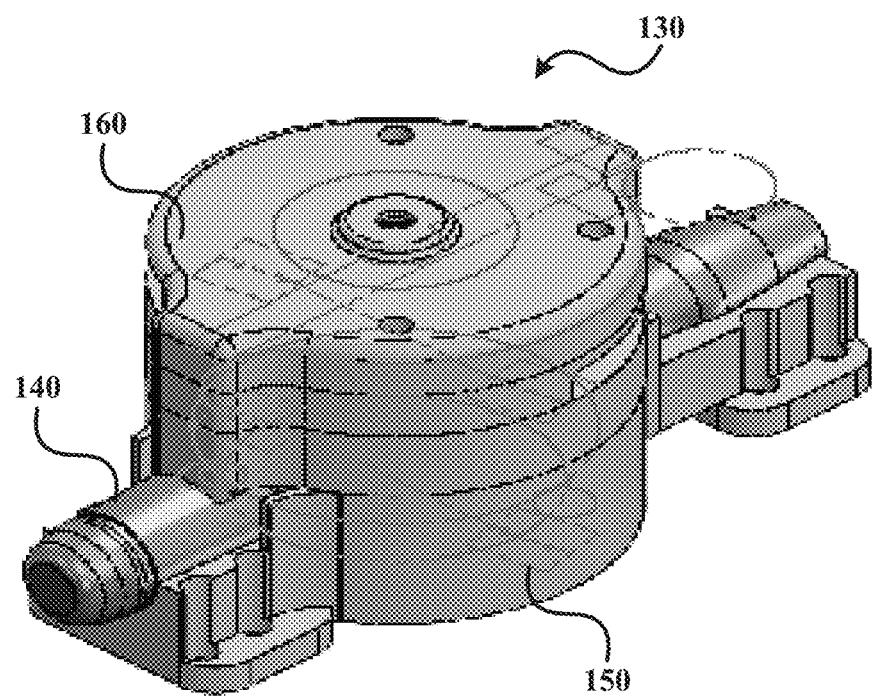

FIG. 7 illustrates a schematic embodiment of the probe handle base and the probe handle cover shown in FIGS. 6A and 6B in accordance with the present invention.

Figure 8A:
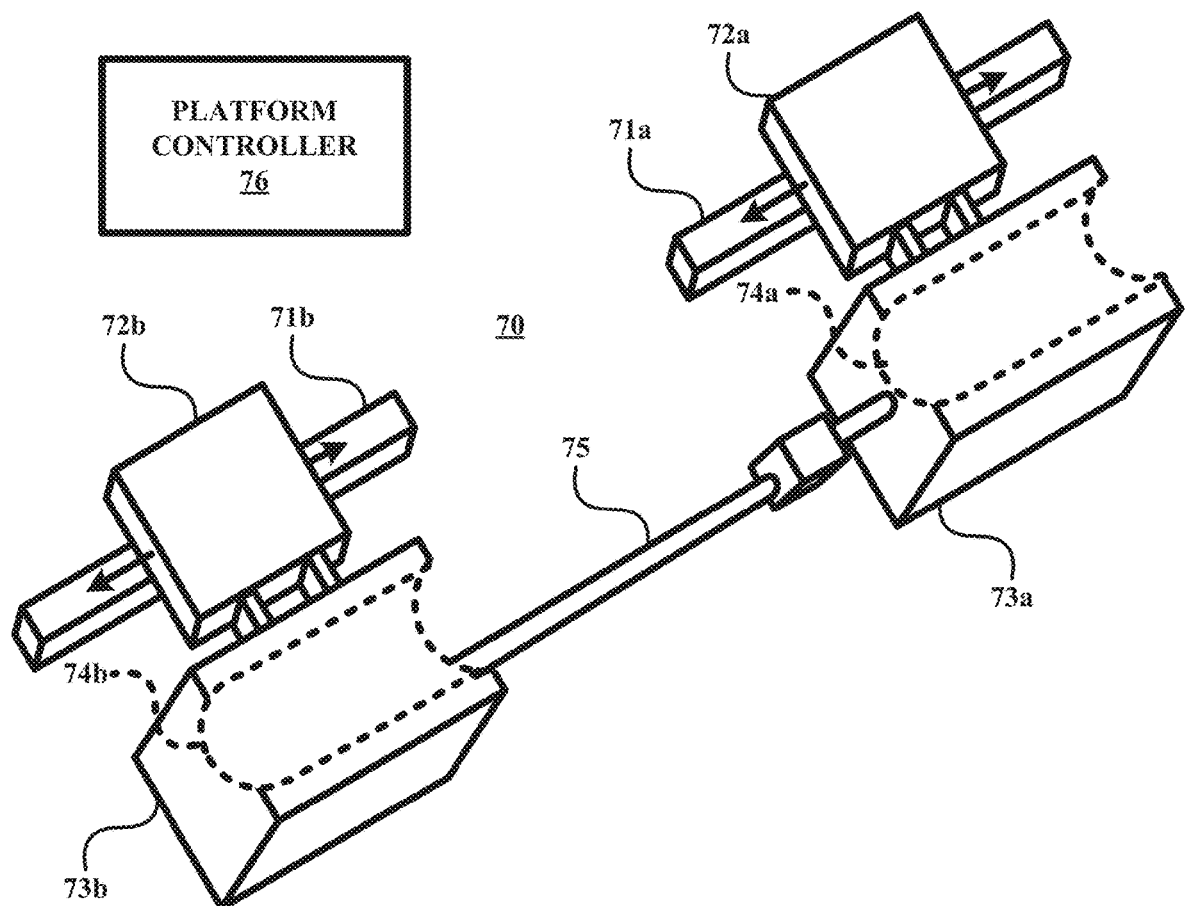
Figure 8B:
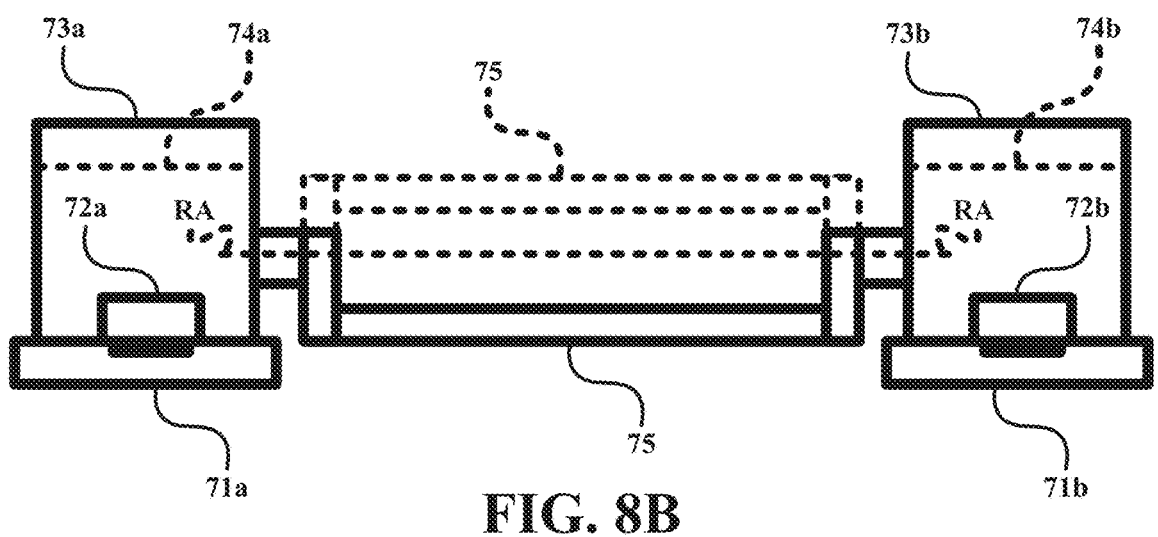

FIGS. 8A and 8B illustrate an exemplary embodiment of an actuator platform in accordance with the present invention.

FIGS. 9A-9D illustrate an operation of the actuator platform shown in FIGS. 8A and 8B.

Figure 10:
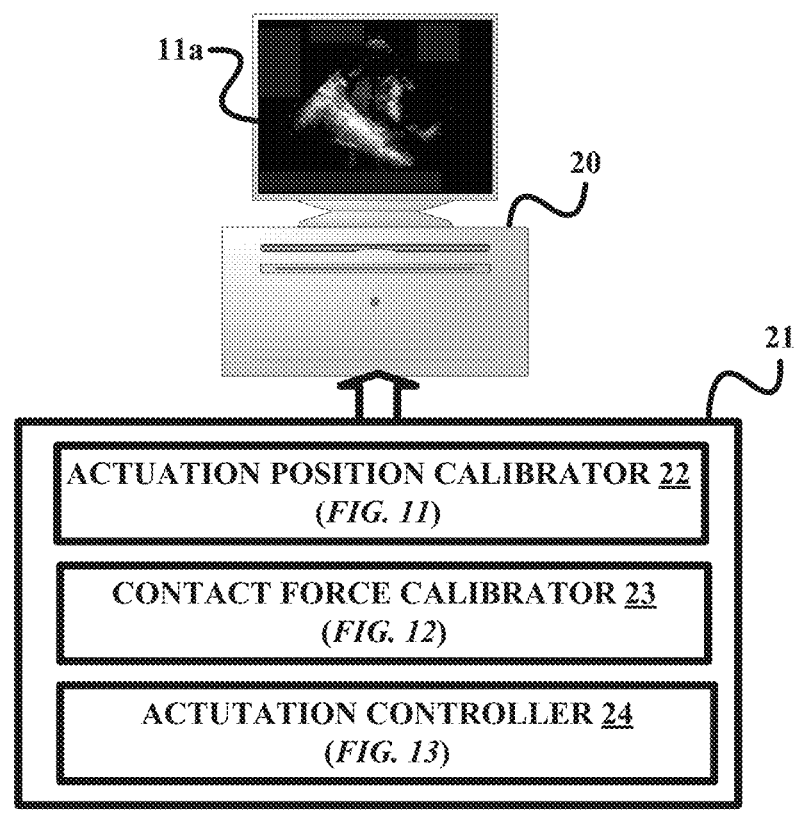

FIG. 10 illustrates an exemplary embodiment of a robotic workstation in accordance with the present invention.

Figure 11:
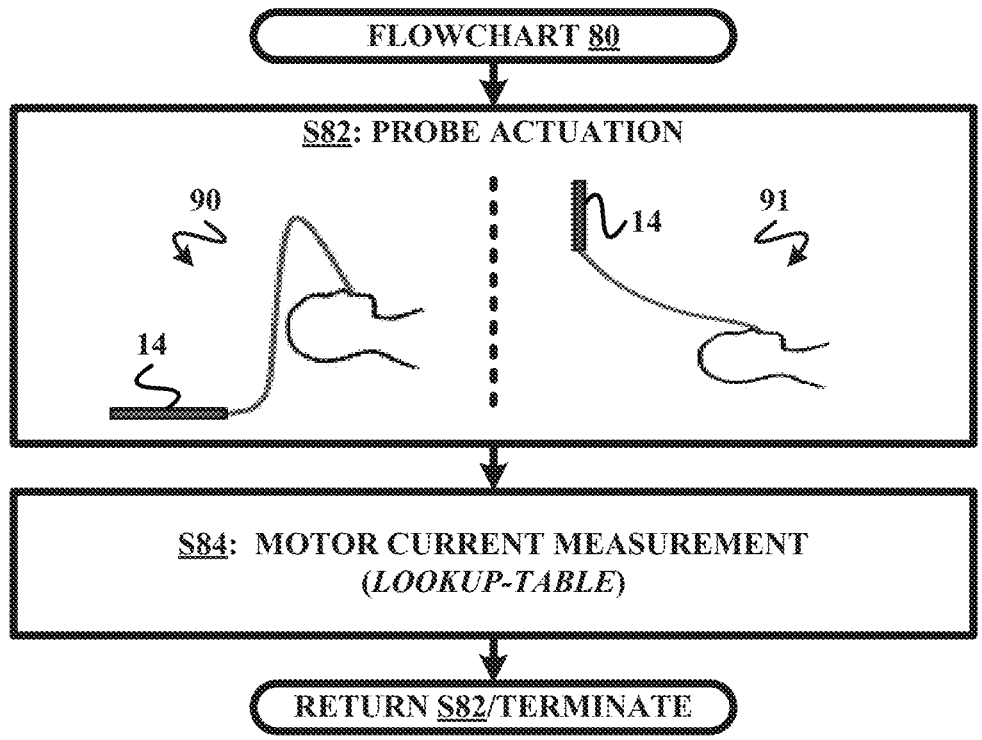

FIG. 11 illustrates a flowchart representative of an exemplary embodiment of an actuation position calibration method in accordance with the present invention.

Figure 12:
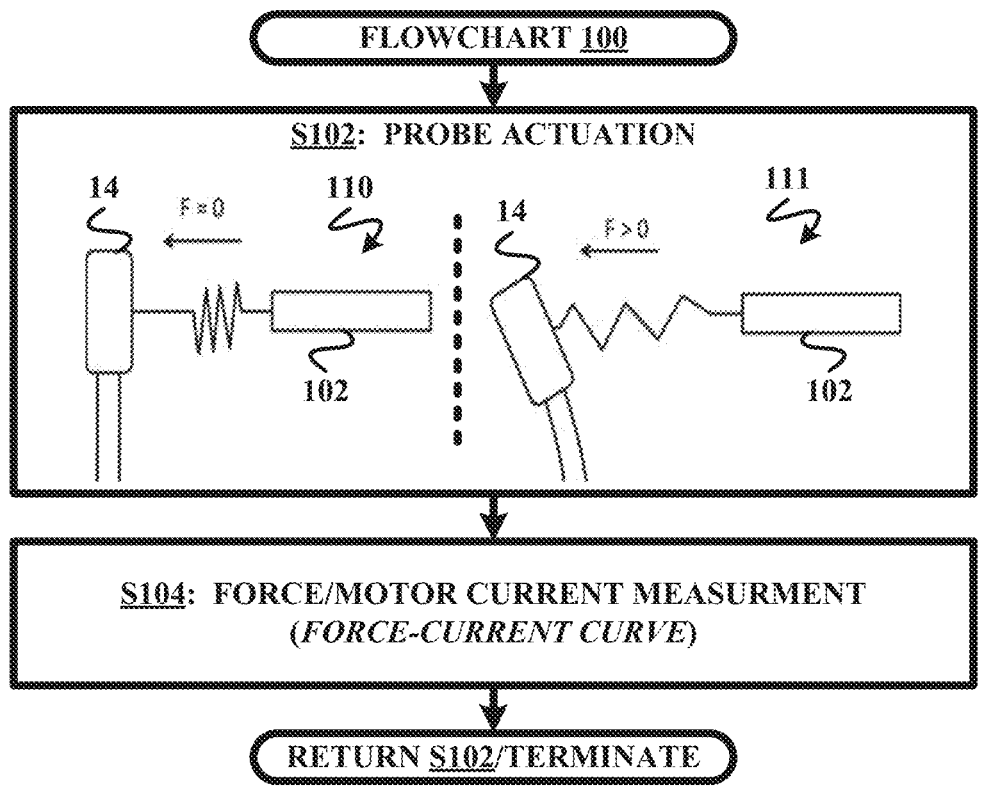

FIG. 12 illustrates a flowchart representative of an exemplary embodiment of a contact force calibration method in accordance with the present invention.

Figure 13:
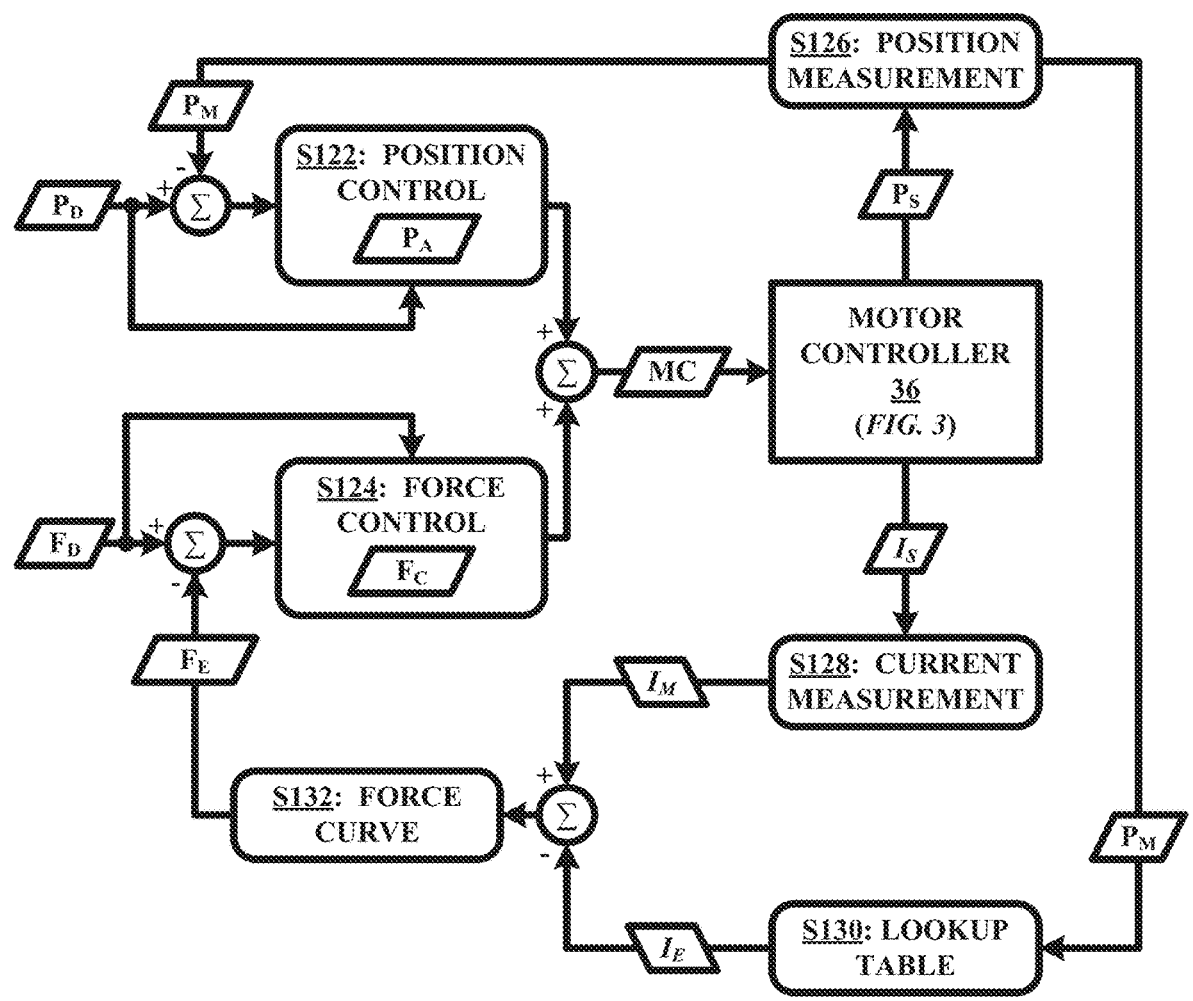

FIG. 13 illustrates an exemplary embodiment of a sensorless force control in accordance with the present invention.

Figure 3:
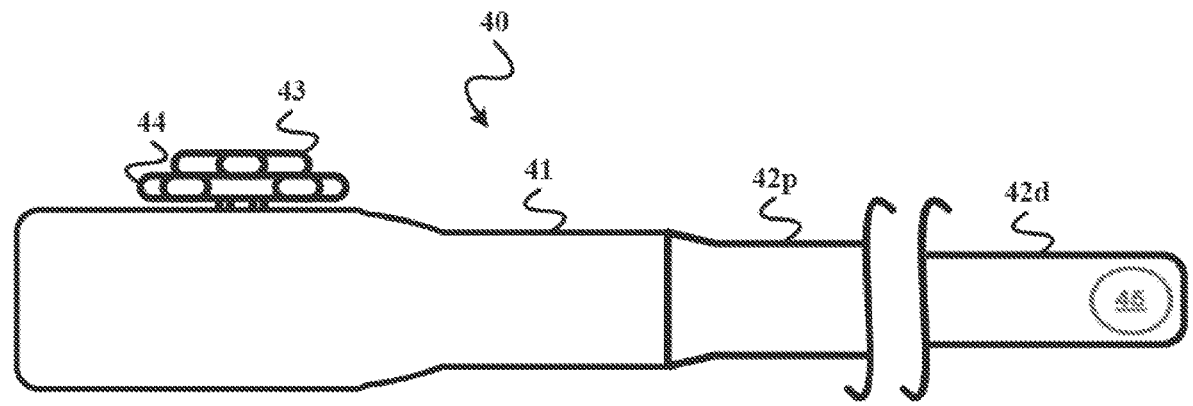
FIG. 3 illustrates an exemplary TEE probe as known in the art.

To facilitate an understanding of the present invention, exemplary embodiments of a robotic actuation system of the present invention and various components therefore will now be described in the context of a remote control actuation of a TEE probe as shown in FIG. 3. From these descriptions, those having ordinary skill in the art will appreciate how to apply the principles of a robotic actuation system of the present invention to any suitable designs of ultrasound probes for any type of procedure as well as other tendon driven flexible devices (e.g., colonoscope, gastroscope, etc.).

Referring to FIG. 3, a TEE probe 40 as known in the art employs a handle 41 and an elongated probe having a proximal end 42p attached to handle 41 and a distal head end 42d with an ultrasound transducer 45. TEE probe 40 employs a yaw actuation dial 43 for adjusting a yaw degree freedom of probe head 42d, and a pitch actuation dial 44 for adjusting a pitch degree freedom of probe head 42d.

Figure 4A:
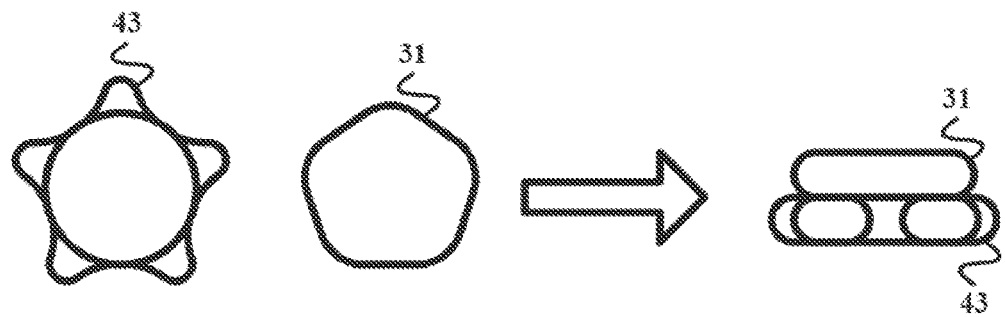
FIGS. 4A and 4B illustrate exemplary engagements of an actuation dial of the TEE probe shown in FIG. 3 and a motorized gear in accordance with the present invention.
Figure 4B:
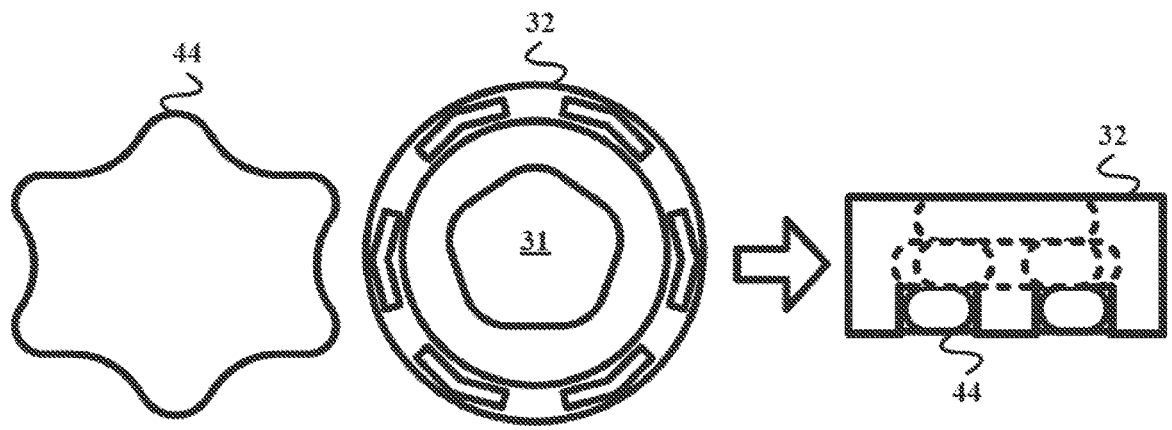

The present invention provides gears that are motorized to control an actuation of yaw actuation dial 43 and pitch actuation dial 44. For example, as shown in FIG. 4A, a friction gear 31 of the present invention is designed to frictionally engage with yaw actuation dial 43 to transmit sufficient torque for controlling a rotation of yaw actuation dial 43. By further example, as shown in FIG. 4B, a crowned gear 32 of the present invention is designed to mechanically engage with pitch actuation dial 44, without contacting yaw actuation dial 43, for controlling a rotation of pitch actuation dial 44.

Figure 2:
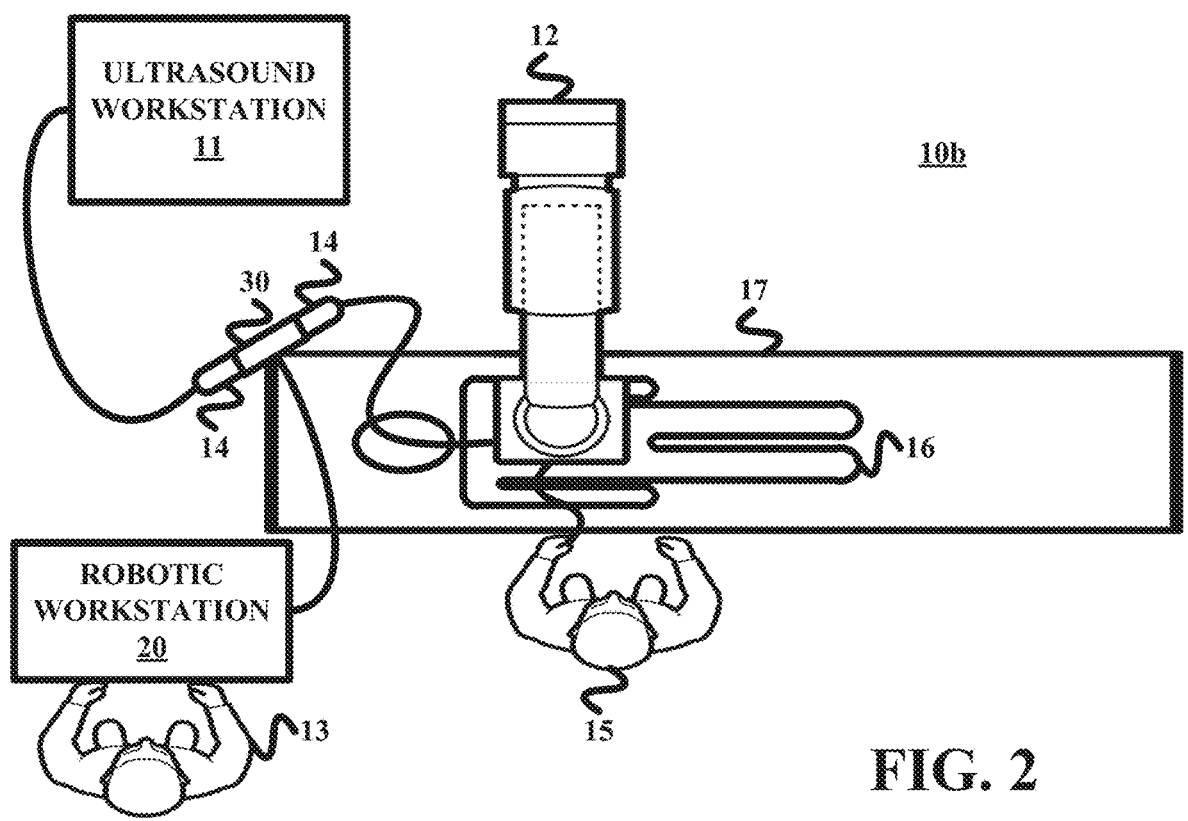
FIG. 2 illustrates an exemplary embodiment of a remote controlled actuation of a TEE probe in accordance with the present invention.

While in practice a design of a gear of robotic actuator 30 (FIG. 2) will be dependent upon a design of a corresponding actuation dial of a probe intended to be engaged thereby, embodiments of robotic actuator 30 will be described herein in the context of gears 31 and 32.

Figure 5:
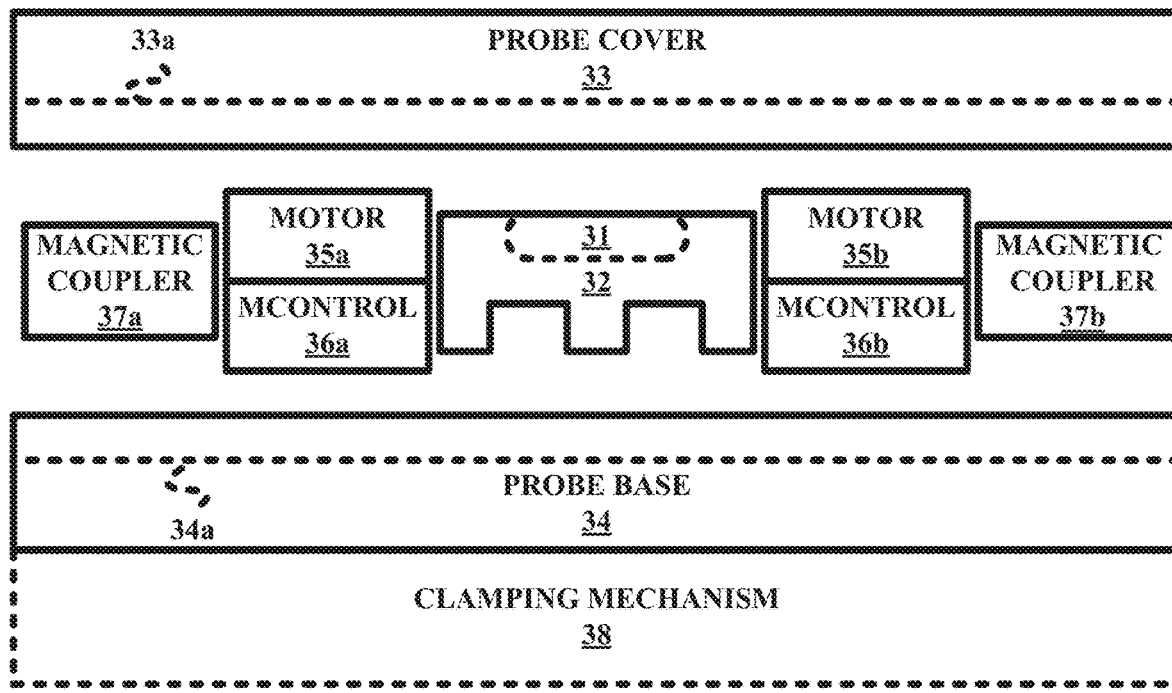
FIG. 5 illustrates an exemplary embodiment of a robotic actuator in accordance with the present invention.

Referring to FIG. 5, one embodiment of robotic actuator 30 employs a probe handle cover 33 having a concave inner surface 33a and a probe handle base 34 having a concave inner surface 34a for defining a actuation chamber upon being magnetically coupled via one or more magnetic couplers, such as, for example, magnetic couplers 37a and 37b as shown. In operation, the chamber houses the actuation dials of the probe and the magnetic coupling provides an advantage of facilitating an easy removal of the probe if desired, particularly if operating circumstances dictate manual control of the probe.

Robotic actuator 30 further employs a motor 35a and a motor controller 36a ("MCONTROLLER") for gear 31 and a motor 35b and a motor controllers 36b for gear 32, which yields motorized gears controllable by robotic workstation 20 (FIG. 2) via an electrical coupling of robotic workstation 20 to motor controllers 36a and 36b. In operation, the motorized gears are sufficient to engage and rotate the actuation dials of the probe, which facilitates a lightweight design of probe handle cover 33.

Additionally, depending upon the environment within robotic actuator 30 is being operated (e.g., an operating room), probe handle base 34 and/or an actuator platform 38 as known in the art may be utilized to secure robotic actuator 30 to a frame of reference within the environment. For example, probe handle base 34 and/or an actuator platform 38 may be mounted to a fixture, an operating table, operating equipment or otherwise any object for securing robotic actuator 30 to a frame of reference within the operating room.

Referring to FIGS. 6A and 6B, a schematic embodiment of robotic actuator 30 employs a probe handle base 50 and a probe handle cover 60 for controlling the actuation dials of a probe (e.g., probe handle 41 as shown). Specifically, probe handle cover 50 has a concave inner surface 51 and probe handle base 60 has a concave inner surface 61 for defining an actuation chamber upon being magnetically coupled via magnetic couplers 52a and 52b of probe handle base 50 and steel locator pins 62a and 62b of probe handle cover 60.

Probe handle base 50 employs motor control boards 53 electrically connected to robotic workstation 20 (FIG. 2), and probe handle cover 60 employs motor control boards 63 electrically connected to motors 64 (e.g., brushed DC motors via two (2) spur gears). Motor control boards 53 and 63 having electrical contacts (not shown)(e.g., spring contacts) that are engaged upon a magnetic coupling of probe handle base 50 and probe handle cover 60 to form motor controllers. Motor controller 53a/63a implements a current control of motor 64a to a crowned gear 65 to thereby control a rotation of crowned gear 65. Similarly, motor controller 53b/63b implements a current control of motor 64b to a friction gear 66 concentric with crowned gear 65 to thereby control a rotation of friction gear 66.

FIG. 7 illustrates an aesthetic practical view of a robotic actuator 130 having a magnetic coupling of a probe handle base 150 and a probe handle cover 160 for housing and controlling actuation dials (not shown) of a probe handle 140.

FIGS. 8A and 8B illustrate one embodiment 70 of actuator platform 38 (FIG. 5) employing a pair of rails 71a and 71b, a pair of sliders 72a and 72b, a pair of rotation motors 73a and 73b, and a crank shaft 75. By techniques known in the art, sliders 72a and 72b are slidably coupled to respective rails 71a and 71b and affixed to respective rotation motors 73a and 73b, and crank shaft 75 is rotatably coupled to rotation motors 73a and 73b. In operation, a platform controller 76 employs hardware, software, firmware and/or circuitry for laterally moving crank shaft 75 via conventional control of a sliding of sliders 72a and 72b along respective rails 71a and 71b in one of the arrow directions and for revolving crank shaft 75 about a rotational axis RA via a control of rotation motors 73a and 73b (e.g., 180° revolution as shown in FIG. 8B). In practice, rotation motors 73a and 73b may have respective groves 74a and 74b for supporting a portion of the probe handle, the probe itself, and/or cabling of the probe.

Figure 9A:
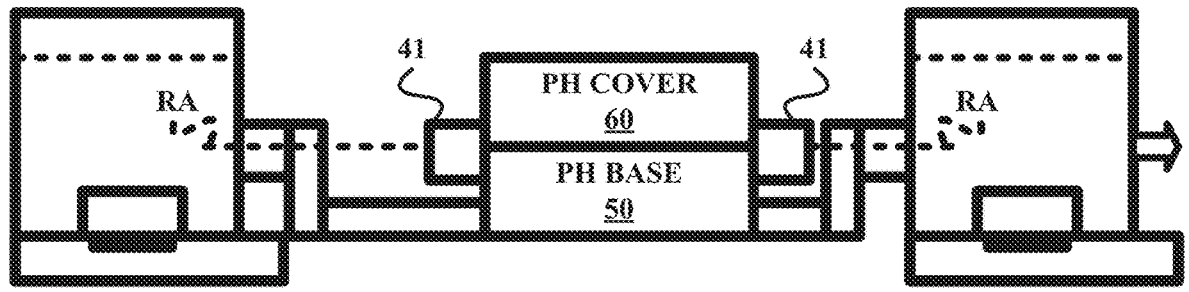
Figure 9B:
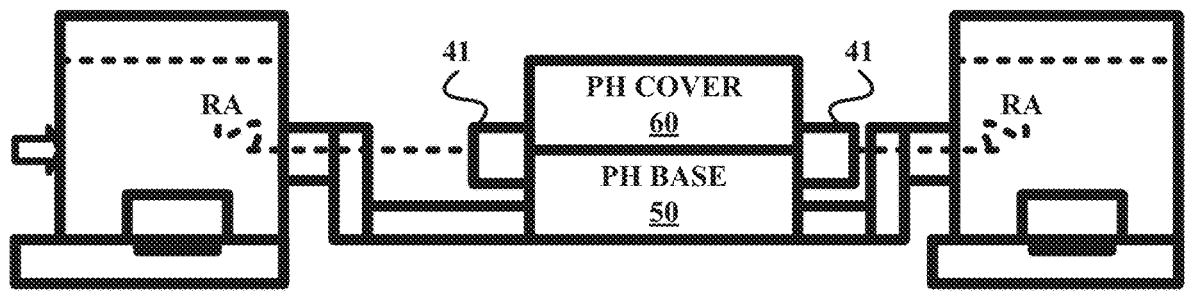
Figure 9C:
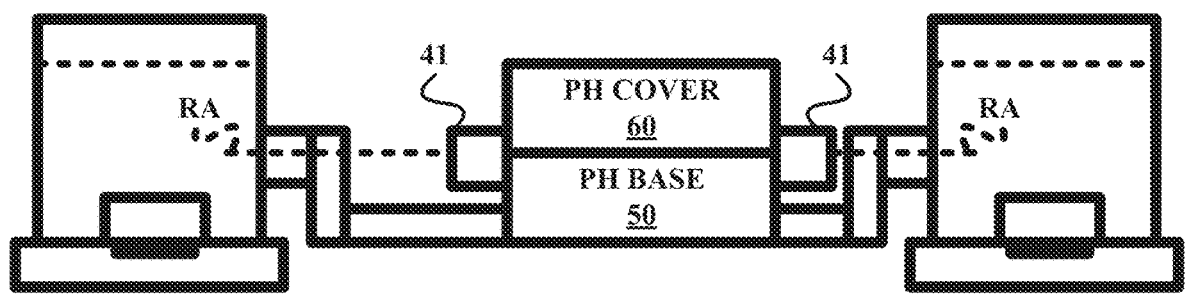
Figure 9D:
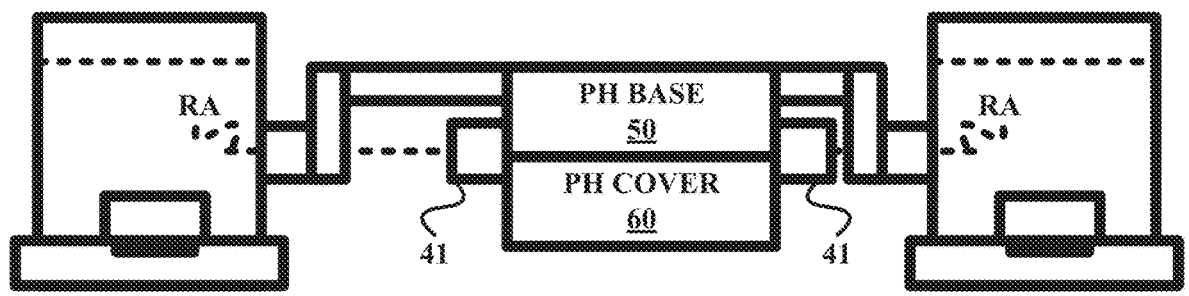

The importance of crank shaft 75 is to maintain a rotational alignment of the probe handle with rotation axis RA as crank shaft 75 is laterally moved as exemplary shown by the arrows in FIGS. 9A and 9B, or is revolved around rotational axis RA as shown in FIGS. 9C and 9D. Specifically, crank shaft 75 extends through probe handle ("PH") base 50 and probe handle 41 as seated between probe handle base 50 and probe handle cover 60 is rotationally aligned with rotational axis RA. As such, lateral movement of crank shaft 75 via control of laterally sliding sliders 72a and 72b on respective rails 71a and 71b will laterally move probe handle 40 in rotationally alignment with rotational axis RA as exemplary shown in FIGS. 9A and 9B. Furthermore, revolving motion of crank shaft around rotational axis RA via control of rotation motors 73a and 73b will rotate probe handle 40 about rotational axis RA as exemplary shown in FIGS. 9C and 9D.

In practice, actuator platform 70 as shown in FIG. 7 provides an additional two (2) degrees for freedom of lateral motion and rotational motion for a distal head 42d of probe 40 capable of being pitched and/or yawed.

Figure 1:
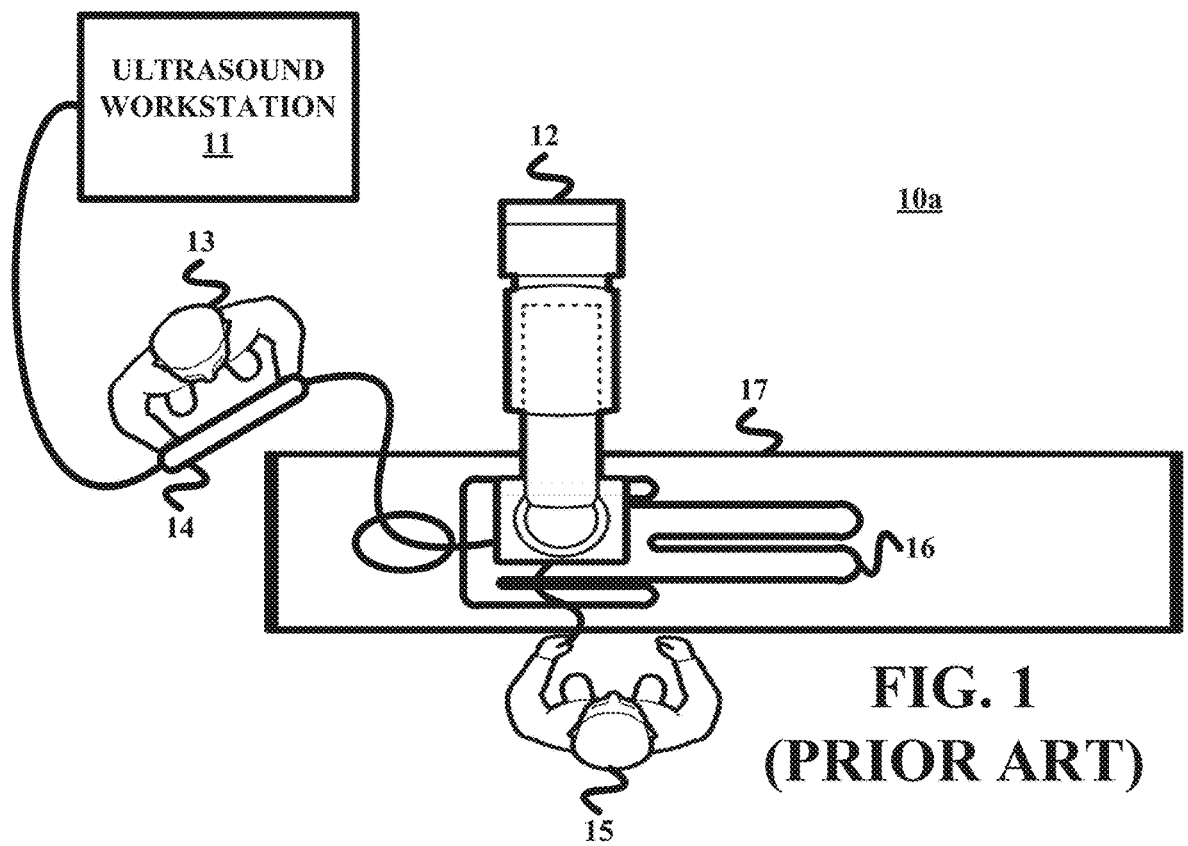
FIG. 1 illustrates an exemplary manual actuation of a TEE probe as known in the art.

Referring back to FIG. 1, robotic workstation 20 is structurally configured with hardware, software, firmware and/or circuitry as known in the art for executing technique(s) to generate motor commands to the motorized gear of robotic actuator 30 via user input. In practice, robotic workstation 20 may implement any known technique(s) for generating motor commands for a particular actuation scheme of a subject probe. More particularly to TEE probe 14, robotic workstation 20 executes known technique(s) for generating the motor commands to control a pitch degree of freedom and a yaw degree of freedom of a distal head of probe 14. Additionally, if actuator platform 70 or any other actuator platform facilitating lateral motion and rotational motion of the distal head of probe 14, the controller of the actuator platform may be a stand-alone controller, coupled to robotic workstation 20 or incorporated within robotic workstation 20. When the controller of the actuator platform is coupled to or incorporated within robotic workstation 20, robotic workstation 20 is structurally configured with hardware, software, firmware and/or circuitry as known in the art for executing known technique(s) to generate motion commands to the controller of the actuator platform via user input.

Also in practice, robotic workstation 20 may implement known component(s) and scheme(s) for interfacing with one or more users of the robotic actuation system. More particularly to FIG. 1, in a direct control scheme, robotic workstation 20 employs appropriate user interfaces (not shown) (e.g., joystick, mouse, touch-screen, etc.) for facilitating direct control of the head of TEE probe 14 by echocardiographer 13. In a collaborative control scheme, robotic workstation 20 employs appropriate user interfaces (not shown) (e.g., joystick, mouse, touch-screen, etc.) for facilitating shared control of the head of TEE probe 14 by echocardiographer 13 and cardiologist 15.

Referring to FIG. 10, robotic workstation 20 is structurally configured with hardware, software, firmware and/or circuitry in accordance with the present invention for generating motor commands to robotic actuator 30 (FIG. 2) for controlling an actuation of TEE probe 14 (FIG. 2) for acquiring ultrasound images 11a. In practice, robotic workstation 20 may execute any technique(s) suitable for the generation of such motor commands.

In one embodiment, robotic workstation 30 employs a network 21 of modules 22-24 installed therein for incorporating a sensorless force control scheme of the present invention involving (1) probe calibration methods to establish an operational relationship between a position/shape of a head of TEE probe 14 and motor currents of robotic actuator 30 and (2) a simultaneous actuation position and force contact of the TEE probe 14. Of importance is the one-to-one correspondence of angular positions of gears 31 and 32 to angular positions of respective actuation dials 42 and 43 as exemplary shown in FIGS. 4A and 4B.

Referring to FIG. 11, a flowchart 80 represents an actuation position calibration method of the present invention executed by an actuation position calibrator 22 (FIG. 10). A stage S82 of flowchart 80 encompasses calibrator 22 initiating a probe actuation cycle of TEE probe 14 by robotic actuator 30 and a stage S84 of flowchart 80 encompasses a measurement of motor current by robotic actuator 30 that is communicated to calibrator 22.

Specifically, for stage S82, TEE probe 14 may be positioned in a plurality of configurations, of which two (2) possible shape configurations 90 and 91 are shown. Specifically, configuration 90 entails TEE probe 14 being mounted parallel to an operating table (not shown) or configuration 91 entails TEE probe 14 being mounted perpendicular to the operating table. For either configuration, TEE probe 14 is allowed to move freely whereby there is no additional force exerted on the head of TEE probe 14, which keeps the head straight.

The probe calibration cycle involves robotic actuator 30 moving the head of TEE probe 14 over a full degree range of a first degree of freedom for numerous degrees of a second degree of freedom at specified degree sample rate(s). As related to TEE probe 14, robotic actuator 30 rotates the yaw actuation dial over a full range of angular positions for numerous angular positions of the pitch actuation dial at a specified sample rate. For example, at a calibration sampling rate of five (5) degrees and a full range of −90 degrees to 90 degrees, robotic actuator 30 rotates yaw actuation dial every five (5) degrees over the full range for each fifth degree of angular position of the pitch actuation dial.

Each sampling involves a measurement and storage of motor current of each motor of robotic actuator 30. To facilitate the sensorless force control, stage S84 may entail a generation of a lookup table of the measured motor currents. The following TABLE is an exemplary lookup table for 649 entries derived from a range of motion)^2/ (sampling rate)^2+1 number of elements (please note only ten (10) selected entries are shown):

| YAW DIAL (DEGREES) | PITCH DIAL (DEGREES) | YAW MOTOR CURRENT (mA) | PITCH MOTOR CURRENT (mA) |
| --- | --- | --- | --- |
| −90 | −90 | 256 | 195 |
| ... | ... | ... | ... |
| 0 | 0 | 0 | 0 |
| 5 | 0 | 87 | 0 |
| 10 | 0 | 96 | 0 |
| ... | ... | ... | ... |
| 0 | 5 | 0 | 43 |
| 0 | 10 | 0 | 65 |
| ... | ... | ... | ... |
| 5 | 5 | 93 | 55 |
| 10 | 5 | 108 | 59 |
| ... | ... | ... | ... |
| 90 | 85 | 254 | 202 |
| 90 | 90 | 259 | 203 |

Calibrator 22 loops through stage S82/S84 until the end of the probe actuation cycle.

Referring to FIG. 12, a flowchart 100 represents a contact force calibration method of the present invention executed by contact force calibrator 23 (FIG. 10). A stage S102 of flowchart 100 encompasses calibrator 23 initiating a probe actuation cycle of TEE probe 14 by robotic actuator 30 as previously described herein for stage S82 of flowchart 80 (FIG. 11) and a stage S104 of flowchart 100 encompasses a measurement of force by a force sensor that is communicated to calibrator 23, which in turns generates a force/motor current ratio.

Specifically, for stage S102, the head of TEE probe 14 is attached to two (2) force sensors through two (2) springs of known mechanical properties. One force sensor is attached perpendicular to the probe head, such as for example, a force sensor 102 attached perpendicular to the head of TEE probe 14 as shown in FIG. 12. The other force sensor (not shown) is attached in plane with the probe head. The springs are configured so that the force is zero when the probe head has a straight configuration 110 and is nonzero when the probe head has a bent configuration (e.g., bent configuration 111).

Values for motor currents and force are recorded during stage S104. It is expected that the current force values will form a hysteresis curve for each degree-of-freedom, which allows a line to be fitted to these values to ensure that there is one force/motor current ratio accurate for facilitating a contact force control as subsequently explained herein.

Calibrator 23 loops through stage S102/S104 until the end of the probe actuation cycle.

Referring to FIG. 13, an actuation controller 24 (FIG. 10) implements a control scheme 120 of a simultaneous actuation position and contact force control. Basically, a desired actuation position $P_D$ of the head of TEE probe 14 is communicated to controller 24 by a user of robotic workstation 20 via a joystick, keyboard or any other input device to position control, which in response thereto controller 24 during a position control stage S122 generates an actuation position $P_A$ for TEE probe 14 in terms of a specific pitch and/or yaw of the head of TEE probe 14 achieved by corresponding angular positions of the gears/actuation dials. Additionally, a desired force $F_D$ of TEE probe 14, which is typically a constant value greater than zero to maintain contact with tissue and ensure acoustic coupling, is communicated to controller 24 during a force control stage S124 whereby controller 24 generates a contact force correction $F_C$ for actuation position $P_A$ for TEE probe 14.

The generation of motor commands MC involves an application of contact force correction $F_C$ to actuation position $P_A$ in view of minimizing a position error between actuation position PA and measured motor positions $P_M$, and a contract force error between desired contact force $F_D$ $F_C$ and an expected contact force $F_E$.

Specifically, motor controller 36 (FIG. 5) of robotic actuator 40 continually communicates sensed motor positions $P_S$ and sensed motor currents $I_S$ during respective stages S126 and S128 of scheme 120 to controller 24. In response thereto, controller 24 periodically measures sensed motor positions $P_S$ and compares the measured motor positions $P_M$ to motor positions associated with a desired actuation position $P_D$ of the head of TEE probe 14 and the resulting position error is an input for position control stage S122 designed to minimize the position error. In practice, controller 24 may execute any control technique(s) as known in the art for minimizing the position error (e.g., a PID control).

Controller 24 also periodically in sync measures sensed motor currents $I_S$ and combines the measured sensed motor currents $I_S$ to an expected motor currents $I_E$, which is calculated by inputting measured motor positions $P_M$ into the lookup table of stage S130 as generated by calibrator 22 (FIG. 11). The lookup table takes two inputs of position of the two dials and returns two (2) expected current values $I_E$ for each degree-of-freedom. During stage S132, expected current values $I_E$ and the measured motor current values $I_M$ are current fed to force curve (C→F) computed by calibrator 23 (FIG. 12) to estimate an expected contact force $F_E$ on the head of TEE probe 14.

Force control stage S124 receives contact force correction $F_C$ from a comparison of desired contact force $F_D$ and expected contract force $F_E$ and adjusts a path generated by position control stage S122 to limit the forces exerted by the head of TEE probe 14. In one embodiment, a direct method to model this motion is to assume that contact surface acts as an ideal spring, in which case:

$$\Delta f = K(x - xo)$$

where $\Delta f$ is the force error signal, x is the position of the contact point, xo would be the position of TEE probe 14 if there was no obstacle, and K is elastic constant of the esophagus of the patient (values known in literature can be used). Since $x_0$ can be known from the kinematic model of TEE probe 14, there is a direct link between motor commands and the force. Similarly to position control value:

$$x = \frac{\Delta f}{K} + x0$$

Controller 24 will continually loop through the stages of scheme 120 during the procedure.

Referring to FIGS. 2-13, those having ordinary skill in the art will appreciate numerous benefits of the present invention including, but not limited to, a sensorless force control for any procedure involving a cable driven interventional tool (e.g., a TEE probe, a steerable catheter, a guidewire, a colonoscope, etc.).

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A robotic actuation system for sensorless force control of an interventional tool having cable driven distal end, the robotic actuation system comprising:
   a robotic actuator operable to control the interventional tool over a range of actuation positions,
      wherein the robotic actuator includes at least one motorized gear operable to operate the cable drive of the interventional tool; and
   a robotic workstation operably connected to the at least one motorized gear to generate motor commands for simultaneous actuation position and contact force control of the interventional tool,
      wherein the robotic workstation is operable to generate the motor commands as a function of an actuation position measurement and a motor current measurement of the at least one motorized gear for a desired actuation position of the interventional tool.

2. The robotic actuation system of claim 1, wherein the robotic workstation generates a motor position error as a function of a comparison of a measured motor position of each at least one motorized gear to a desired motor position of each at least one motorized gear associated with the desired actuation position of the interventional tool.

3. The robotic actuation system of claim 1, wherein the robotic workstation generates a contact force error as a function of a comparison of an expected motor current of the motorized gear to a desired motor current of the motorized gear.

4. The robotic actuation system of claim 1,
   wherein the robotic workstation generates a motor position error as a function of a comparison of a measured motor position of each at least one motorized gear to a desired motor position of each at least one motorized gear associated with the desired actuation position of the interventional tool;
   wherein the robotic workstation generates a contact force error as a function of a comparison of an expected motor current of the motorized gear to a desired motor current of the motorized gear; and
   wherein the motor commands are generated by the robotic workstation to minimize the motor position error and the force error.

5. The robotic actuation system of claim 3,
   wherein the robotic workstation includes a calibration lookup table of expected motor currents for a measured motor position of each at least one motorized gear;
   wherein the robotic workstation includes a calibration curve including a force-to-motor current curve for the interventional tool; and
   wherein the robotic workstation derives the expected contact force of the interventional tool from the calibration lookup table and the calibration curve.

6. The robotic actuation system of claim 5, wherein the robotic workstation inputs the measured motor position of each at least one motorized gear into the calibration lookup table to output at least one expected motor current.

7. The robotic actuation system of claim 6, wherein the robotic workstation applies the at least one expected motor current and a measured motor current of each at least one motorized gear to the calibration curve to output the expected contact force of the interventional tool.

8. The robotic actuation system of claim 1, wherein the interventional tool is one of a cable driven group of interventional tools including a probe, a steerable catheter, a guidewire and a colonoscope.

9. The robotic actuation system of claim 1, wherein the robot actuator further includes:
   a coupling of a handle base and a handle cover to define an actuation chamber for housing an engagement of the at least one motorized gear to a handle of the interventional tool.

* * * * *